US00PP37270P2

(12) United States Plant Patent
Ackerman et al.

(10) Patent No.: US PP37,270 P2
(45) Date of Patent: Feb. 17, 2026

(54) STRAWBERRY PLANT NAMED 'PE-14.250.070'

(50) Latin Name: ***Fragaria* x *ananassa***
Varietal Denomination: PE-14.250.070

(71) Applicant: PLANT SCIENCES, INC., Watsonville, CA (US)

(72) Inventors: Stephen M. Ackerman, Salinas, CA (US); Steven D. Nelson, Watsonville, CA (US); Michael D. Nelson, Watsonville, CA (US)

(73) Assignee: Plant Sciences, Inc., Watsonville, CA (US)

( * ) Notice: Subject to any disclaimer, the term of this patent is extended or adjusted under 35 U.S.C. 154(b) by 0 days.

(21) Appl. No.: 19/053,365

(22) Filed: Feb. 13, 2025

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./209, 208
CPC ..... A01H 5/08; A01H 5/00; A01H 6/7409; A01H 6/74
See application file for complete search history.

(56) References Cited

U.S. PATENT DOCUMENTS

PP28,756 P3 12/2017 Ackerman et al.

*Primary Examiner* — June Hwu
(74) *Attorney, Agent, or Firm* — Foley & Lardner LLP

(57) ABSTRACT

This invention relates to a new and distinct variety of strawberry plant named 'PE-14.250.070'. This new strawberry plant named 'PE-14.250.070' is primarily adapted to the growing conditions of the central coast of California, and is primarily characterized by its orange red fruit color, medium fruit size, conical fruit shape, with very slight differences between fruits; very attractive fruit with good sweetness, medium flesh firmness, and seeds held even to slightly below the surface; large size plant which produces an abundance of runners; medium size foliage, dark yellow green colored foliage, concave shaped foliage, with three to four leaflets per leaf; and fruiting trusses with little to no anthocyanins, which are medium in length, and typically held below the foliage.

5 Drawing Sheets

Latin name of the genus and species of the plant claimed: *Fragaria* x *ananassa.*
Variety denomination: 'PE-14.250.070'.

BACKGROUND OF THE INVENTION

The present invention relates to a new and distinct strawberry variety named 'PE-14.250.070'. This new variety is a result of a controlled cross made in 2014 in an ongoing breeding program between strawberry selection designated 'PS-8.1120' (not patented) as the seed (female) parent, and strawberry selection designated 'PE-7.2064' (not patented) as the pollen (male) parent. The variety is botanically known as *Fragaria* x *ananassa.*

The seedling resulting from the aforementioned cross was selected from a controlled breeding plot in Ventura County, California in the fall of 2016. After its selection, the new variety was asexually propagated by stolons in the city of Macdoel, Siskiyou County and in Manteca, San Joaquin County, California. The new variety was tested extensively over the next several years in fruiting fields in Ventura County, California. This propagation has demonstrated that the combination of traits disclosed herein as characterizing the new variety are fixed and remain true-to-type through successive generations of asexual reproduction.

BRIEF SUMMARY OF THE INVENTION

'PE-14.250.070' is primarily adapted to the climate and growing conditions of the central coast of California. The nearby Pacific Ocean provides the humidity and moderate temperatures needed to produce a strong, vigorous plant and maintain fruit quality during the fall production months.

The following traits have been repeatedly observed and are determined to be unique characteristics of 'PE-14.250.070', which in combination distinguish this strawberry plant as a new and distinct variety:

1. Fruit is orange red in color, medium in size, conical in shape, with very slight differences between fruits;
2. Fruit is very attractive with good sweetness, has medium flesh firmness, with seeds held even to slightly below the surface;
3. Plant is large in size and produces an abundance of runners;
4. Foliage is medium in size, dark yellow green in color, slightly concave in shape, and produces three to four leaflets per leaf; and
5. Fruiting trusses have little to no anthocyanins, are medium in length, and typically held below the foliage.

The strawberry variety that is believed to be most closely related to the new variety 'PE-14.250.070' is 'PE-7.2059' (U.S. Plant Pat. No. 28,756). In side-by-side comparisons to the similar strawberry variety 'PE-7.2059' (U.S. Plant Pat. No. 28,756), 'PE-14.250.070' differs by the following combination of characteristics as described in Table 1.

TABLE 1

| Characteristic | 'PE-14.250.070' | 'PE-7.2059' (U.S. Plant Pat. No. 28,756) |
|---|---|---|
| Fruit: color | Orange red | Red |
| Fruit: size | Medium | Large |
| Fruit: market yield, season average (grams/plant) | 628 | 563 |
| Fruit: firmness of flesh | Medium | Firm |
| Fruit: insertion of achenes | Ranges from level with to below the surface | Ranges from level with to above the surface |
| Plant: size | Large | Medium |
| Foliage: color of upper surface | Dark yellow green | Medium green |
| Foliage: rugosity | Medium | Strong |
| Fruiting truss: length | Medium | Short |
| Disease: Fusarium wilt | Resistant | Susceptible |

For identification, a series of molecular markers have been determined for this new variety.

'PE-14.250.070' differs from its parents, 'PS-8.1120' (not patented) and 'PE-7.2064' (not patented) by the following combination of characteristics as described in Tables 2 and 3.

TABLE 2

| Characteristic | 'PE-14.250.070' | 'PS-8.1120' (not patented) |
|---|---|---|
| Fruit: size | Medium | Large |
| Fruit: color | Orange red | Red |
| Fruit: sweetness | Good | Very good |
| Fruit: firmness of flesh | Medium | Firm |
| Plant: size | Large | Medium |

TABLE 3

| Characteristic | 'PE-14.250.070' | 'PE-7.2064' (not patented) |
|---|---|---|
| Fruit: size | Medium | Small |
| Fruit: flavor | Good | Fair |
| Fruit: firmness of flesh | Medium | Firm |
| Plant: size | Large | Medium |
| Stolon: quantity | Many | Medium |

BRIEF DESCRIPTIONS OF THE PHOTOGRAPHS

The accompanying color photographs illustrate the overall appearance of typical specimens of the new strawberry variety 'PE-14.250.070' at various stages of development, as true as it is reasonably possible with color reproductions of this type. Color in the photographs may differ slightly from the color value cited in the botanical descriptions which accurately describe the color of 'PE-14.250.070'. The depicted plant and plant parts of the new strawberry variety 'PE-14.250.070' are approximately three to four months old. The photographs were taken in Ventura County, California.

DETAILED BOTANICAL DESCRIPTION

Figure 1:
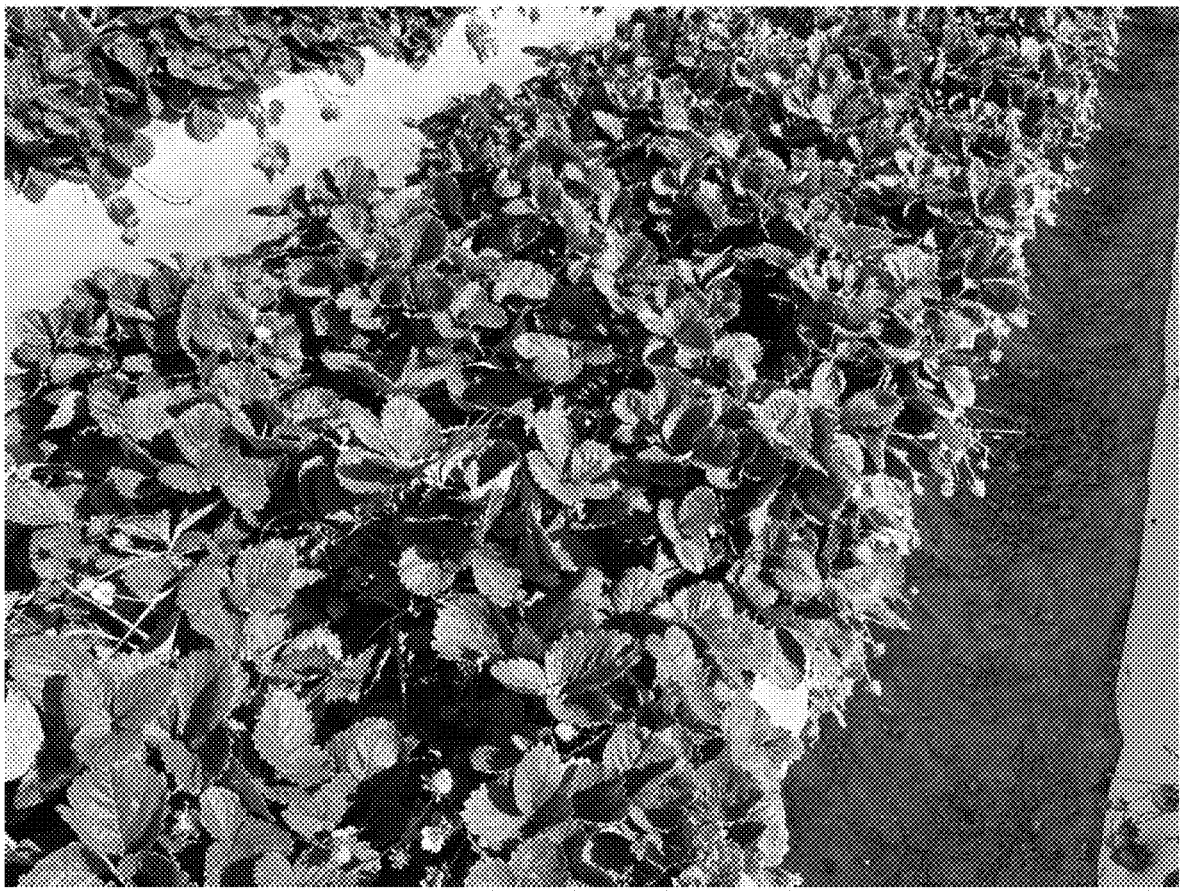
FIG. 1 shows fruiting field characteristics of 'PE-14.250.070', taken in the month of October 2024.
Figure 2:
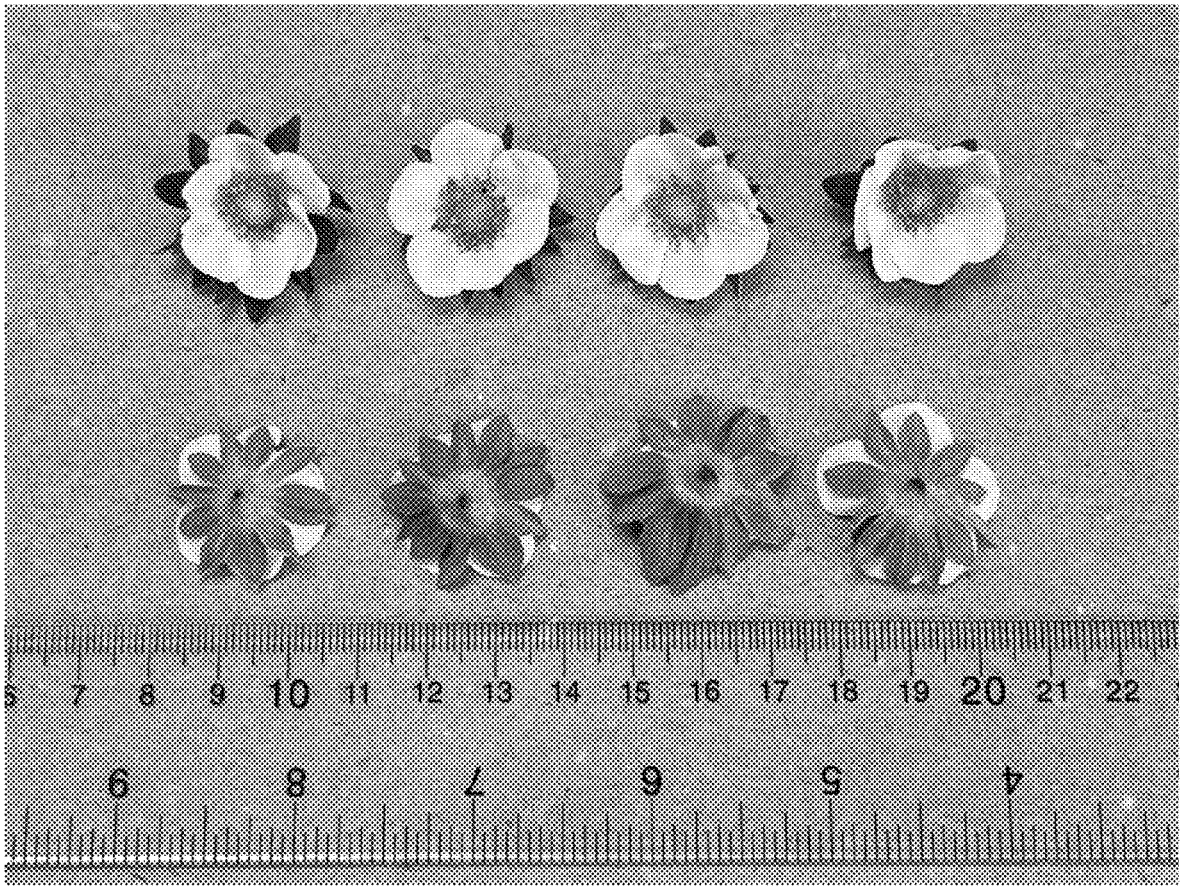
FIG. 2 shows upper and lower surfaces of flower and flower parts of 'PE-14.250.070', taken in the month of October 2024.
Figure 3:
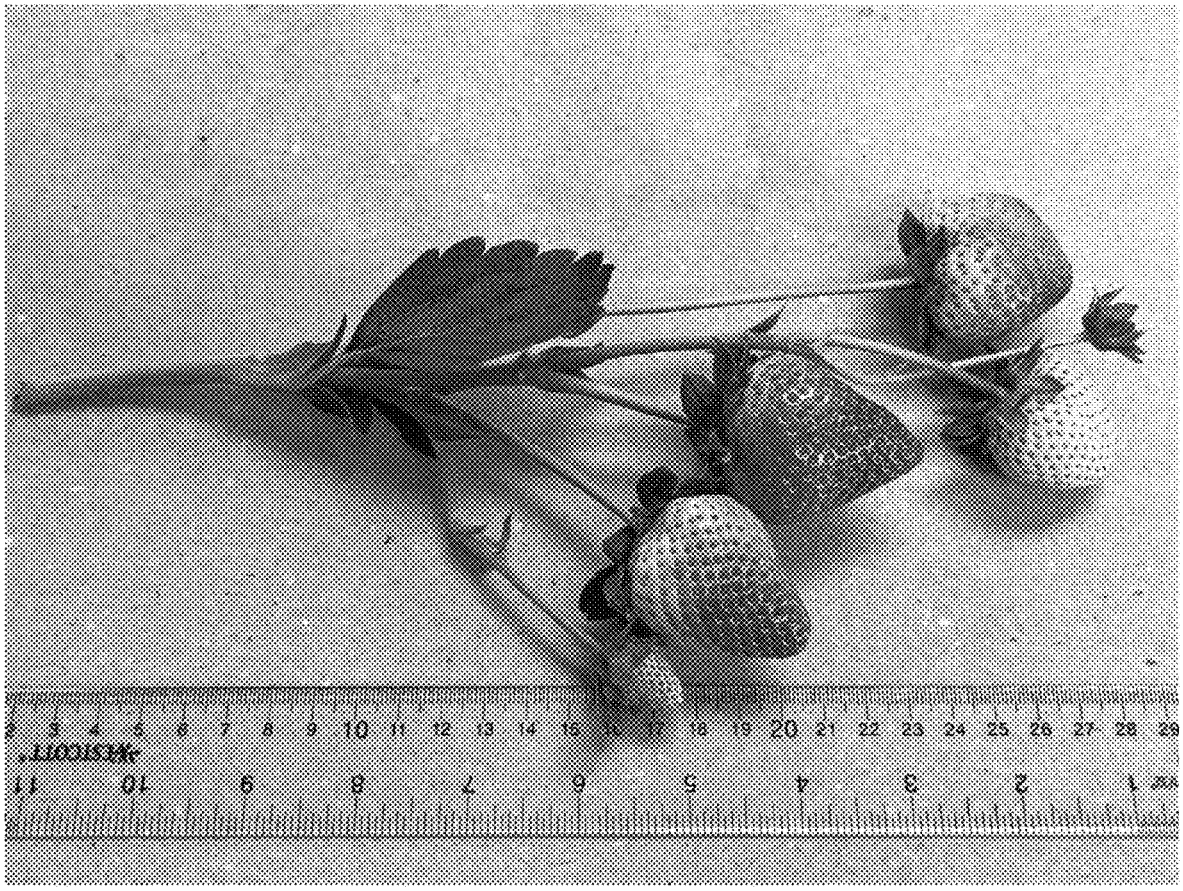
FIG. 3 shows typical fruiting truss and truss parts of 'PE-14.250.070', taken in the month of October 2024.
Figure 4:
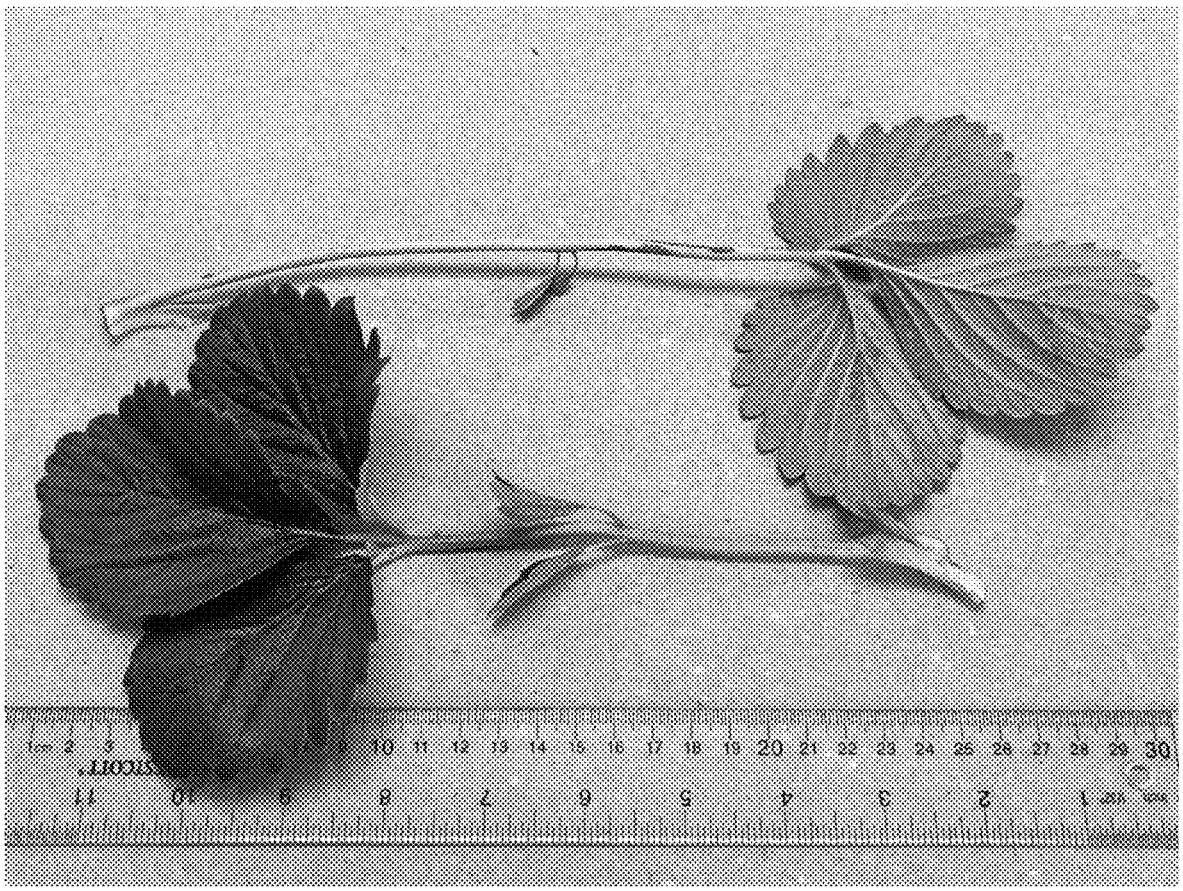
FIG. 4 shows upper and lower surfaces of leaf and leaf parts of 'PE-14.250.070', taken in the month of October 2024.
Figure 5:
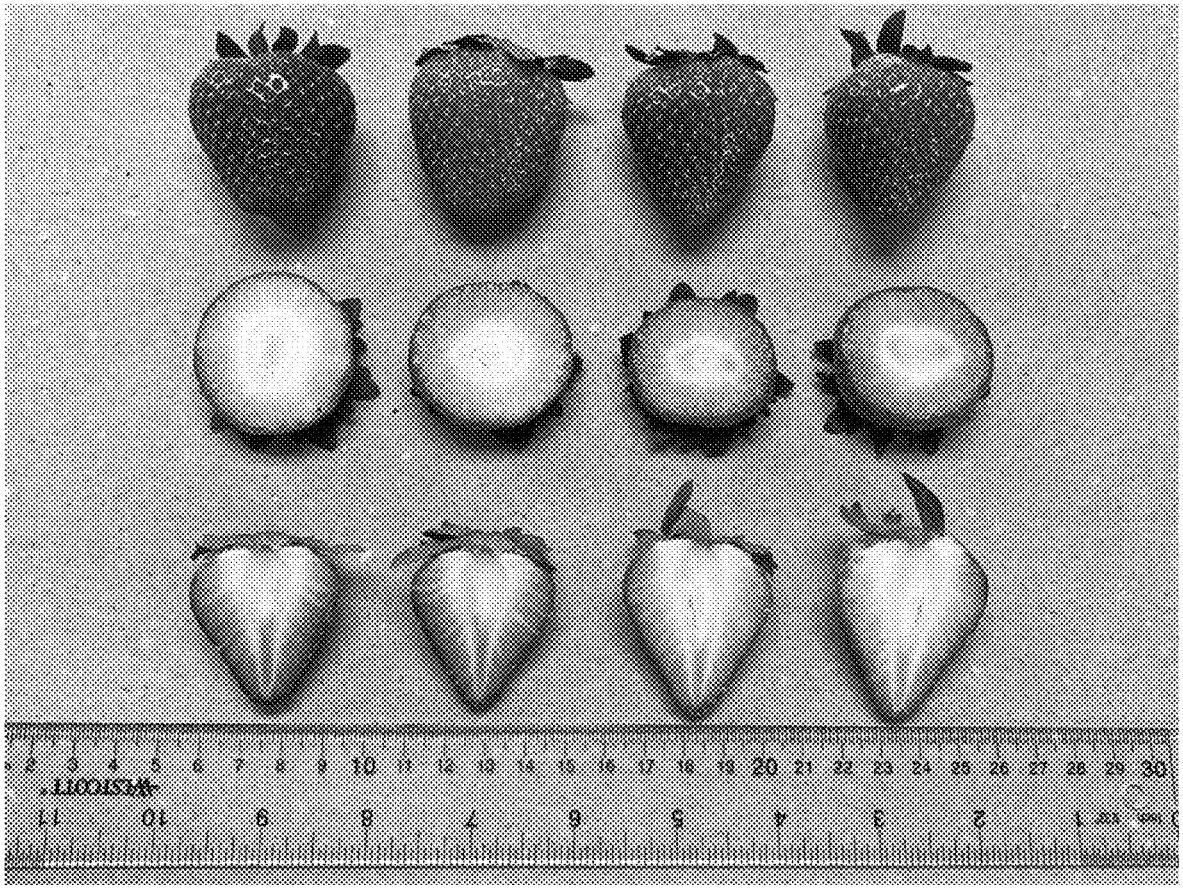
FIG. 5 shows internal and external mature fruit characteristics of 'PE-14.250.070', taken in the month of October 2024.

The new variety 'PE-14.250.070' has not been observed under all possible environmental conditions. The characteristics of the new variety 'PE-14.250.070' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'PE-14.250.070', unless otherwise noted, are based on observations taken during the 2024 growing season in Ventura County, California. These measurements and ratings were taken from plants of 'PE-14.250.070' dug from a low-elevation nursery located in San Joaquin County, California in January 2024 and planted approximately six months later in Ventura County, California. The approximate age of the observed plants is three to four months. Yield observations including average weight and marketable yield, along with fruit quality characteristics including soluble solids, are averaged from four years of data collected from the 2021 through 2024 growing seasons. Flower measurements and characteristics are from secondary flowers unless otherwise noted. Fruit characteristics and measurements are from secondary fruit, unless otherwise noted.

Where noted, color terminology follows the Royal Horticultural Society Colour Chart, London, Sixth Edition (2015).

The following characteristics describe fruit, plant, stolon, foliage, fruiting truss, flower, reproductive organs and pest and disease characteristics of the new strawberry 'PE-14.250.070'.

Fruit characteristics:

*Color of mature fruit*.—RHS 44A (orange red).
*Color of internal flesh*.—RHS 44C (light red).
*Color of core*.—RHS 43C (light red).
*Average length* (*cm*).—4.0.
*Average width* (*cm*).—3.7.
*Size*.—Medium.
*Average length/width ratio*.—1.09 (slightly longer than broad).
*Fruit shape at apex*.—Obtuse.
*Fruit shape at calyx*.—Flattened.
*Hollow center average length* (*mm*).—4.2.
*Hollow center average width* (*mm*).—0.9.
*Hollow center expression*.—Absent or very weak.
*Season average weight* (*gm*).—23.8.
*Marketable yield season* (*gm/plant*).—628.
*Predominant shape*.—Conical.
*Difference in shape between primary and secondary fruit*.—None or very slight.
*Band without achenes*.—Narrow.
*Evenness of surface*.—Even or very slightly uneven.

*Evenness of color*.—Even or very slightly uneven.
*Glossiness*.—Medium.
*Insertion of achenes*.—Ranges from below surface to level with surface.
*Average calyx diameter* (*cm*).—4.3.
*Position of calyx attachment*.—Level.
*Attitude of sepals*.—Outward.
*Size of calyx in relation to fruit diameter*.—Slightly larger.
*Adherence of calyx* (*when fully ripe*).—Strong.
*Firmness of flesh*.—Medium.
*Keeping quality*.—Very good.
*Fruit market*.—Fresh.
*Post-harvest fruit longevity* (at 1 to 3 *degrees Celsius*).—7 to 10 days.
*Distribution of red color of the flesh*.—Marginal and central.
*Sweetness*.—Good.
*Soluble solids* (% *Brix*).—7.4.
*Achene color, shaded side*.—RHS 160A (greyed yellow group).
*Achene color, sun-exposed side*.—RHS 182B (greyed red group).
*Achene average length* (*mm*).—1.7.
*Achene average width* (*mm*).—0.8.
*Achene average weight* (*mg*).—0.53.
*Achene average quantity per berry*.—292.
*Achene shape*.—Elliptic.
*Time of beginning of flowering* (50% *of plants with at least one flower*).—Medium (August in Ventura County, California).
*Time of beginning of fruit ripening* (50% *of plants with mature fruit*).—Medium (September in Ventura County, California).
*Flowering season*.—August to December (in Ventura County, California).
*Harvest season*.—September to January (in Ventura County, California).
*Harvest maturity*.—Mid (October).
*Plant hardiness*.—Zone 10 (USDA Plant Hardiness Zone Map).
*Type of bearing*.—Fully remontant (non-flowering runners).

Plant characteristics:
*Average height* (*cm*).—25.8.
*Average spread* (*cm*).—38.6.
*Size*.—Large.
*Habit*.—Semi-upright.
*Density of foliage*.—Medium.
*Vigor*.—Strong.

Stolon characteristics:
*Color*.—RHS 146C (yellow green group).
*Anthocyanin coloration*.—RHS 180C (orange red group).
*Anthocyanin intensity*.—Weak.
*Pubescence*.—Dense.
*Attitude of hairs*.—Slightly outward.
*Average quantity in nursery* (*per square foot*).—5 to 6 (medium).
*Average diameter at first bract* (*mm*).—4.1 (thick).
*Length from mother plant to first daughter* (*cm*).—27.0.

Terminal leaflet characteristics:
*Average length* (*cm*).—9.2
*Average width* (*cm*).—7.9.
*Average area terminal* (*cm*2).—72.8.
*Average length/width ratio*.—1.16 (longer than broad).
*Shape of base*.—Acute.
*Shape of apex*.—Obtuse.
*Margins* (*shape of teeth*).—Obtuse (serrate to crenate).
*Average serrations per leaf*.—20.2.

Foliage characteristics:
*Color of upper surface*.—RHS 147A (dark yellow green).
*Color of lower surface*.—RHS 147C (yellow green group).
*Color of venation, upper surface*.—RHS 144B (yellow green group).
*Color of venation, lower surface*.—RHS 145A (yellow green group).
*Number of leaflets*.—3 to 4.
*Leaf size*.—Medium.
*Average length* (*cm*).—16.1.
*Average width* (*cm*).—17.7.
*Average area foliage* (*cm*2).—287.0.
*Shape in cross section*.—Slightly concave.
*Interveinal blistering*.—Medium.
*Pubescence of upper surface*.—Medium.
*Pubescence of lower surface*.—None.
*Venation pattern*.—Pinnate reticulate.
*Leaf glossiness*.—Medium.
*Leaf variegation*.—Absent.
*Leaf rugosity*.—Medium.

Petiole characteristics:
*Petiole color*.—RHS 144B (yellow green group).
*Petiole average length* (*cm*).—17.2.
*Petiole average diameter* (*mm*).—4.0.
*Petiole size*.—Medium.
*Attitude of hairs*.—Slightly outward.
*Frequency of bract leaflets*.—72% occurrence (mostly).
*Size of bract leaflets*.—Medium.
*Pubescence*.—Moderate.
*Petiolule color*.—RHS 144B (yellow green group).
*Petiolule average length* (*mm*).—13.4.
*Petiolule average diameter* (*mm*).—2.2.

Stipule characteristics:
*Color*.—RHS 146D (yellow green group).
*Anthocyanin coloration*.—RHS 63A (red purple group).
*Anthocyanin intensity*.—Absent or very weak.
*Average length* (*mm*).—22.1.
*Average width* (*mm*).—9.4.
*Shape*.—Triangular.
*Pubescence*.—Light.
*Shape of base*.—N/A.
*Shape of apex*.—Acuminate.

Fruiting truss characteristics:
*Anthocyanin coloration*.—RHS 184D (greyed purple group).
*Anthocyanin intensity*.—Absent or very weak.
*Average length at maturity* (*cm*).—29.7.
*Position relative to foliage*.—Strongly below.
*Flower quantity* (*season average per plant*).—30 to 35 (medium).
*Average fruit quantity per truss*.—7.3 (medium).
*Attitude at first pick*.—Prostrate.
*Primary pedicel color*.—RHS 144B (yellow green group).
*Primary pedicel average length* (*cm*).—7.2.
*Primary pedicel average diameter* (*mm*).—3.3.

*Pedicel attitude of hairs*.—Slightly outward.
*Pedicel pubescence*.—Dense.
*Primary peduncle color*.—RHS 144B (yellow green group).
*Primary peduncle average length* (*cm*).—9.6.
*Primary peduncle average diameter* (*mm*).—5.1.
*Peduncle pubescence*.—Dense.

Flower characteristics (secondary unless indicated):
*Petal color, upper surface*.—RHS NN155C (white group).
*Petal color, lower surface*.—RHS NN155C (white group).
*Petal average length* (*mm*).—11.0.
*Petal average width* (*mm*).—10.9.
*Petal average length/width ratio*.—1.02 (as long as broad).
*Average petal quantity per flower*.—5.8.
*Petal shape*.—Obovate.
*Petal pubescence*.—None.
*Petal shape of base*.—Obtuse.
*Petal shape of apex*.—Rotund.
*Sepal color, upper surface*.—RHS NN137A (green group).
*Sepal color, lower surface*.—RHS 138A (green group).
*Sepal average length* (*mm*).—10.3.
*Sepal average width* (*mm*).—4.6.
*Sepal average length/width ratio*.—2.25.
*Average sepal quantity per flower*.—11.7.
*Sepal shape*.—Elliptical.
*Sepal pubescence*.—Light.
*Sepal shape of apex*.—Acute.
*Flower bud color*.—RHS 145A (yellow green group).
*Flower bud shape*.—Pyriform.
*Flower bud average length* (*mm*).—16.6.
*Flower bud average diameter* (*mm*).—7.6.
*Corolla average diameter* (*mm*).—28.6 (medium).
*Flower average depth* (*mm*).—11.8 (medium).
*Calyx average diameter* (*mm*).—29.5.
*Size of calyx relative to corolla*.—Same size.
*Arrangement of petals*.—Overlapping.
*Size of inner calyx relative to outer calyx*.—Same.

Reproductive organs:
*Anther color*.—RHS 14A (yellow orange group).
*Filament color*.—RHS 145C (yellow green group).
*Stamen*.—Present.
*Filament average length* (*mm*).—2.6.
*Anther average length* (*mm*).—1.2.
*Anther average width* (*mm*).—0.9.
*Anther shape*.—Elliptic.
*Pollen color*.—RHS 14A (yellow orange group).
*Pollen amount*.—Abundant.
*Ovary color*.—RHS 148B (yellow green group).
*Style color*.—RHS 151D (yellow green group).
*Pistil average quantity per flower*.—292.
*Pistil average length* (*mm*).—1.3.
*Style average length* (*mm*).—1.1.
*Stigma average diameter* (*mm*).—0.16.
*Stigma shape*.—Rounded.

Disease and pest reactions:
*Powdery mildew* (*Sphaerotheca macularis*).—Moderately resistant.
*Botrytis fruit rot* (*Botrytis cinerea*).—Moderate.
*Fusarium wilt* (*Fusarium oxysporum*).—Resistant.
*Two-spotted spider mite* (*Tetranychus urticae*).—Moderate.

We claim:

1. A new and distinct strawberry plant named 'PE-14.250.070', as herein described and illustrated.

* * * * *